United States Patent [19]

Lees

[11] Patent Number: 4,877,599

[45] Date of Patent: Oct. 31, 1989

[54] DETECTION OF VASCULAR DISEASE WITH LABELLED ANTIBODIES

[75] Inventor: Robert S. Lees, Brookline, Mass.

[73] Assignee: New England Deaconess Hospital Corporation, Boston, Mass.

[21] Appl. No.: 220,376

[22] Filed: Jul. 11, 1988

Related U.S. Application Data

[63] Continuation of Ser. No. 929,012, Nov. 10, 1986, abandoned.

[51] Int. Cl.$^4$ .................... A61K 49/02; A61K 49/00; C07K 17/00
[52] U.S. Cl. .......................................... 424/1.1; 424/9; 424/85.8; 514/824; 436/548; 530/402
[58] Field of Search .................... 424/1.1, 9, 85.8, 85; 514/824; 436/548; 530/402

[56] References Cited

U.S. PATENT DOCUMENTS

| | | | |
|---|---|---|---|
| 4,116,776 | 9/1978 | Dalbow et al. | 424/1.1 X |
| 4,311,688 | 1/1982 | Burchiel et al. | 424/1 |
| 4,323,546 | 4/1982 | Crockford et al. | 424/1 |
| 4,331,647 | 5/1982 | Goldenberg | 424/1 |
| 4,348,376 | 9/1982 | Goldenberg et al. | 424/1 |
| 4,359,453 | 11/1982 | Gordon | 424/1.1 |
| 4,427,371 | 9/1984 | Burchiel et al. | 424/1.1 |
| 4,443,427 | 4/1984 | Reinherz et al. | 424/1.1 |
| 4,451,570 | 5/1984 | Royston et al. | 435/240 |
| 4,478,815 | 10/1984 | Burchiel et al. | 424/1.1 |
| 4,529,694 | 7/1985 | Lazarus et al. | 435/172 |
| 4,577,636 | 3/1986 | Spears | 424/1.1 X |
| 4,605,413 | 8/1986 | Urry et al. | 530/329 X |
| 4,647,445 | 3/1987 | Lees | 424/1.1 |
| 4,660,563 | 4/1987 | Lees | 128/654 |
| 4,675,287 | 6/1987 | Reisfeld et al. | 436/519 X |
| 4,681,782 | 7/1987 | Ozkan | 436/529 X |

FOREIGN PATENT DOCUMENTS 137457 4/1984 European Pat. Off. .
163041 3/1985 European Pat. Off. .
189688 8/1986 European Pat. Off. .

OTHER PUBLICATIONS

Scearce et al., *Methods in Enzymology*, vol. 103, pp. 459–469 (1983).
Meares et al., *Anayltical Biochemistry*, vol. 142, pp. 68–78 (1984).
McFarlane, *Nature*, vol. 182, No. 4267, p. 53.
Zurawski et al., *Monoclonal Antibodies* (Kennett Ed. 1980), pp. 19–20.
Oi et al., *Selected Methods in Cellular Immunology* (Mishell Ed. 1980), pp. 353–372.
Khaw et al., *Science*, vol. 209, pp. 295–297 (1980).
Khaw et al., *J. Nuclear Medicine*, vol. 23, No. 11 (1982), pp. 1011–1019.
Hnatowich, *Science*, vol. 220, pp. 613–615 (1983).

*Primary Examiner*—John S. Maples
*Attorney, Agent, or Firm*—Lahive & Cockfield

[57] ABSTRACT

Vascular diseases including asymptomatic atherosclerosis can be diagnosed by administering a conjugate diagnostic reagent to a patient and then detecting the location and concentration of the conjugate reagent within the patient's vascular system. The conjugate reagents have a target-seeking, biologically active molecule as one component and a labeling means capable of extracorporeal detection as the other component. The biologically active molecules (BAMs) are chosen to have affinity for structural elements of the arterial wall which are either not present in the normal wall but are found in atherosclerotic or arteritic lesions, or which are not available to the blood-borne reagent within normal arterial walls, but are exposed to the reagent in atherosclerotic or arteriotic lesions.

17 Claims, No Drawings

DETECTION OF VASCULAR DISEASE WITH LABELLED ANTIBODIES

The U.S. Government has rights in this invention pursuant to NIH Grant No. RO1HL32975.

This application is a continuation, of application Ser. No. 929,012, filed Nov. 10, 1986, now abandoned.

BACKGROUND

The technical field of this invention concerns methods and means for detecting vascular diseases, such as atherosclerotic lesions, and in particular, methods and means employing labeled, target-seeking, biologically active molecules to detect abnormal arterial structures or compositions.

Atherosclerosis is a disease which causes the thickening and hardening of the arteries, particularly the larger artery walls. It is characterized by lesions of raised fibrous plaque which form within the arterial lumen. The plaques are most prevalent in the abdominal aorta, coronary arteries or carotid arteries and they increase progressively with age. They commonly present dome-shaped, opaque, glistening surfaces which bulge into the lumen. A lesion typically will consist of a central core of lipid and necrotic cell debris, capped by a collagen fibromuscular layer. Complicated lesions will also include calcified deposits and exhibit various degrees of necrosis, thrombosis and ulceration.

The deformities of the arterial lumen presented by the plaque and associated deposits result in occluded blood flow, and ultimately ischemic heart disease, stroke, or diseases of other organs, if untreated. At present, coronary atherosclerosis is still the leading cause of death in the United States, claiming the lives of over a half million Americans annually, roughly twice as many as are killed by cancer.

Unfortunately, the early stages of atherosclerosis and related vascular diseases are most often clinically silent. Since lifestyle changes, drug therapy and other means exist for delaying or reducing vascular occlusion or the stresses on various body organs which result from atherosclerotic lesions, the early detection of atheromatous plaque in the vascular system would be of considerable value in permitting preventive intervention at a time when it can be most effective.

Arteriography, the conventional approach to assessing vascular disease, involves catheterization and the injection of radioopaque substances into the bloodstream in order to image obstructions in the arteries. This procedure involves significant morbidity, in that infection, perforation of the artery, arrhythmia, stroke, infarction and even death can occur. Because of the risks involved, arteriograms typically are reserved for individuals with advanced or acute atherosclerotic disease.

A variety of less invasive techniques for the diagnosis of vascular diseases have been proposed. These techniques include plethysmography, thermography and ultrasonic scanning For a further review of these techniques, see an article by the present inventor and a colleague, Lees and Myers, "Non-Invasive Diagnosis of Arterial Disease", Vol. 27 *Annals of Internal Medicine*, pp. 475–509 (1982), herein incorporated by reference.

Another non-invasive approach to the diagnosis of vascular disease which has been proposed by the present inventor involves the labeling of low density lipoproteins (LDLs) with radioisotopes and the administration of such labeled LDLs to a patient. Because atherosclerotic plaques tend to take up lipoproteins from the blood circulating in the arteries, the labeled LDLs can be imaged with a gamma camera or other radiation detector to provide information on the location and extent of plaque in the vascular system. For details on this approach, see U.S. Pat. No. 4,660,563 "Method and Means for Detection of Arterial Lesions" dated Apr. 29, 19 and U.S. Pat. No. 4,647,445 "Improved Radiolabelled Lipoproteins and Methods for Making Same" dated Mar. 3, 1987, both of which are also incorporated herein by reference.

One disadvantage to the use of labeled LDL's is that the patient's own blood typically is the most appropriate source of lipoproteins, and this entails a two or three day delay between the beginning and the end of the study. Often, such a time period is not available for sick patients. Furthermore, labeled LDLs image acute, rapidly growing atherosclerosic lesions, as reported by the present inventor and colleagues, Lees et al., *Journal of Nuclear Medicine*, Vol. 24, pp. 154–156, 1983, and herein incorporated by reference. The need exists to localize less rapidly growing artherosclerosic lesions which may not take up LDLs rapidly enough to be imaged. Consequently, there exists a need for better non-invasive techniques and reagents capable of detecting vascular diseases, locating arterial lesions and quantifying the extent of vascular injury.

SUMMARY OF THE INVENTION

Vascular diseases, including asymptomatic atherosclerosis, can be diagnosed by administering a conjugate diagnostic reagent to a patient and then detecting the location and concentration of the conjugate reagent within the patient's vascular system. The conjugate reagents have a target-seeking, biologically active molecule as one component and a labeling means capable of extracorporeal detection as the other component. The biologically active molecules (BAMs) are chosen to have affinity for structural elements of the arterial wall which are either not present in the normal wall but are found in atherosclerotic lesions, or which are not available to the blood-borne reagent within normal arterial walls, but are exposed to the reagent in atherosclerotic lesions.

In particular, the invention encompasses conjugates of radionuclides with various antibodies or fragments thereof which have affinity for certain arterial wall components which are exposed to the blood in atherosclerosis. Two conjugated reagents having particularly useful BAMs are disclosed. The BAMs have high affinity for elastin and chondroitin sulfate proteoglycans (CSPG), respectively. The conjugates of the present invention can be administered individually or in conjunction with each other.

Suitable radionuclides include Co-57, Cu-67, Ga-67, Ga-68, Ru-97, Tc-99m, In-111, In-113m, I-123, I-125, I-131, Hg-197, Au-198, and Pb-203. The BAMs and radionuclides can be linked by direct labeling (e.g., by acidic buffered reactions or oxidative procedures) or by ligand exchange or chelation. The radionuclides are preferably imaged with a radiation detection means capable of detecting gamma radiation, such as a gamma camera or the like.

Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The invention can also be practiced with non-radioactive labeling means, such as magnetic contrast agents capable of detection in magnetic resonance imaging (MRI) systems. In such systems, a strong magnetic field is used to align the nuclear spin vectors of the atoms in a patient's body. The field is then disturbed and an image of the patient is read as the nuclei return to their equilibrium alignments. In the present invention, target-seeking BAMs can be linked to diamagnetic contrast agents, such as gadolinium, cobalt, nickel, manganese or copper complexes, to form conjugate diagnostic reagents that are imaged extracorporeally with an MRI system.

The invention will next be described in connection with certain preferred embodiments; however, it should be clear that various changes, additions and subtractions can be made without departing from the spirit or scope of the invention. For example, monoclonal antibodies (or fragments Fab thereof) as well as polyclonal antibodies (or fragments Fab) can be employed as target-seeking, biologically active molecules. Additionally, human antibodies (i.e., obtained from human-human or human-animal hybridomas) can be used as well as animal antibodies.

Moreover, it should be clear that various antigenic determinants can be used to identify atherosclerotic plaque. Although the embodiments that follow describe two such determinants in detail, elastin and chondroitin sulfate proteogylcans (CSPG), it should be clear that other determinants can also be used as targets against which BAMs can be raised and used in conjugate reagents. Such determinants may include, for examples, particular species of collagen and glycoproteins, such as HLA-DR or similar proteins, which have been reported to be present on the surface of atherosclerotic smooth muscle cells.

DETAILED DESCRIPTION

Chemical changes are known to occur in the arterial wall during atherogenesis. Fragmentation of elastin fibers, disruption of endothelial cells, and proliferation of fibroblasts and smooth muscle cells will typically be observed Increased synthesis of collagen and changes in the distribution of collagen types also occur. New capillary ingrowth and the presence of foam cells with large accumulations of cholesterol are also typical.

During the formation of atherosclerotic lesions, the elastin present in the arterial wall becomes enzymatically degraded. This fragmented elastin is chemically different from native elastin. Additionally, the composition of the proteoglycans which coat the arterial wall changes markedly; the content of other proteoglycans decreases and that of chondroitin sulfate proteoglycan increases. These two chemical changes are exploited in the present invention.

In the preferred embodiments of the invention, antibodies are raised against elastin and chondroitin sulfate proteoglycans (CSPG). These antibodies or fragments derived therefrom are then used to create conjugated diagnostic reagents.

The invention will next be described in connection with certain non-limiting examples.

EXAMPLE 1

Antibodies to human elastin were used to image balloon angioplasty-induced lesions in rabbit aorta. The particular antibodies were polyclonal sheep anti-human lung amorphorous elastin antibodies obtained from Dr. J. Rosenbloom of the University of Pennsylvania. Such antibodies can be generated independently by known techniques. For example, human elastin can be isolated from a lung autopsy specimen, emulsified with Freund's complete adjuvant and then injected subcutaneously at multiple sites into a sheep (e.g., 10–20 milligrams). One month later, the animal can be boosted (e.g., with 5 milligrams of the same antigenic preparation), and one week after that, the animal can be bled. The immunoglobulin fraction can be recovered from the whole blood serum by passage through a Protein A-Sepharose affinity chromotography column.

In the present example, the anti-elastin antibodies were labeled with I-125 (i.e., sodium iodide) as described by McFarlane in Vol. 182, *Nature.* p. 53 (1958). Excess I-125 can be dialyzed off against physiological saline solution at a pH of about 8. The I-125 labeled antibody was then injected intravenously (approximately 300 millicuries per animal) in each of three rabbits which had four weeks previously undergone balloon diendothelialization of the abdominal aorta. Twenty-four to forty-eight hours later, the rabbits were sacrificed, the aortas removed, washed with normal saline, cut open lenghtwise, and covered with polyester wrap. The aortas were then carefully placed on a sheet of high speed X-ray film, and the audioradiograph was allowed to develop for four weeks.

The audioradiograph showed clear-cut localization of the elastin on the image at the healing (reendothelization) edge of the aortic lesions produced by the previous trauma. Since this lesion is known to resemble human arteriosclerosis in many important respects, including accumulation of lipoproteins and other pathological changes, the ability of the antiserum to localize at the trauma site and permit the imaging thereof demonstrates the utility of the present invention in imaging vascular disease.

EXAMPLE 2

In a second example, antibodies to human chondroitin sulfate proteoglycan (anti-CSPG) were similarly used to image the abdominal aortas of rabbits which had been previously balloon diendothelialized. The particular antibodies were monoclonal anti-CSPG antibodies obtained from Drs. M. Lark and T. Wight of the University of Washington. Such antibodies can be generated independently by known techniques. For example, monoclonal antibodies or active fragments can be obtained by applying generally known cell fusion techniques (cf. G. Kohler, C. Milstein, Eur. J. Immunol. 6;511–519 (1976) and M. Shulman et al., Nature 276;269–270 (1978)) to obtain a hybridoma producing the antibody, by deriving a monoclonal antibody from the hybridoma and (optionally) by subjecting the monoclonal antibody to proteolysis to obtain the active Fab fragment.

Monoclonal antibodies are prepared by obtaining mammalian lymphocytes (preferably spleen cells), committing the lymphocytes to produce antibodies (e.g., by immunizing the mammal with the particular antigenic determinant of interest beforehand), fusing the lymphocytes with myeloma (or other immortal) cells to form hybrid cells, and then culturing a selected hybrid cell colony in vivo or in vitro to yield antibodies identical in structure and reactivity.

In the particular case of monoclonal antibodies to chondrotin-sulfate proteoglycans (anti-CSPG), such antibodies can be prepared by isolating CSPG from smooth muscle cells in tissue culture. The CSPG can be extracted from the culture medium and purified by ion exchange chromotography. Mice or other animals can be challenged with a solution of the above-derived CSPG in Freund's adjuvant (i.e., 1–5 milligram CSPG per milliliter of medium emulsified with one milliliter of adjuvant) injected into the peritoneal cavities of the animals. Six weeks later a similar injection (without adjuvant) can be administered as a booster.

Approximately ten days later, the mice are killed and their spleens homogenized The spleen cells are hybridized with mouse myeloma cells by the above-referenced procedure of Kohler and Milstein. The hybridomas so produced are screened to select a cell line producing antibodies which react with human aortic chondroitin sulphate proteoglycan. Large scale antibody production can be obtained from such anti-CSPG producing cell lines by various techniques, including the induction of ascites tumors (i.e., after priming with pristane) and the purification of such antibodies from the ascites fluid by Protein A-Sepharose affinity chromotography.

In the present example, the pure IgM antibody was labeled with I-125 by the same method as described in Example 1 and injected into each of three rabbits in a similar manner. Audioradiographs produced as described above clearly showed that the labeled anti-CSPG antibodies imaged the bare, injured areas of the arterial wall and did not image either healthy arterial wall regions or those areas where rapid reendothelialization was occurring. Thus, this antibody can image aspects of vascular disease which are distinct from those detected by the anti-elastin antibodies discussed in Example 1.

EXAMPLE 3

For comparison, three rabbits were similarly treated with non-specific IgG and three rabbits with non-specific IgM. In each case, a similar audioradiograph was made of the animal's aorta 48 hours after injection of the I-125 labeled non-specific immunoglobulins. Only a very faint image of the edges of the legions were seen with these antibodies. The images were in no way similar to the images seen with either of the specific antibodies described above.

For a further description of general hybridoma production methods, see Oi and Herzenberg, "Immunoglobulin-Producing Hybrid Cell Lines" in *Selected Methods in Cellular Immunology* (Mishell and Shiigi, Ed., W.H. Freeman & Co., 1980) and Scearce and Eisenbarth, "Production of Monoclonal Antibodies..." in Vol. 103 *Methods in Enzymology*, pp. 459–469 (1983), herein incorporated by reference. For descriptions of human hybridoma production techniques, see U.S. Pat. No. 4,451,570 issued to Royston et al. on May 29, 1984; U.S. Pat. No. 4,529,694 issued to Lazarus et al. on July 16, 1985 and Zurawski et al, "Continuously Proliferating Human Cell Lines Synthesizing Antibody of Predetermining Specificity" in *Monoclonal Antibodies* (Plenum Press, N.Y. 1980), also incorporated by reference.

Active fragments can be derived from the monoclonal antibodies disclosed herein by a number of techniques. For example, purified monoclonal antibodies can be treated in a buffer solution with an enzyme, such as pepsin and subjected to HPLC gel filtration. The appropriate fraction containing Fab can then be collected and concentrated by membrane filtration or the like. For further description of the general techniques for isolation of active fragments, see for example, Khaw, BA et al., Vol. 23 *J. Nucl. Med.*, pp. 1011–1019 (1982), incorporated by reference.

The antibodies and fragments used herein can be labeled preferably with radioactive labels, by a variety of techniques other than the above-described McFarland technique. For example, the biologically active molecules can also be labeled with a radionuclide via conjugation with the cyclic anhydride of diethylenetriamine penta-acetic acid (DTPA) or bromoacetyl aminobenzyl ethylamine diamine tetra-acidic acid (BABE). See generally Hnatowich et al., Vol. 220 *Science*, pp. 613–315. (1983) and Meares et al. Vol. 142 *Analytical Biochemistry*, pp. 68–78 (1984) incorporated by reference for further description of labeling techniques.

I claim:

1. A conjugated diagnostic reagent having an antibody or fragment thereof with specific affinity for at least one arterial wall component associated with an abnormality of the vascular system, said arterial component being selected from the group consisting of insoluble, cross-linked elastin and insoluble, cross-linked fragments thereof and chondroitin sulfate proteoglycan compounds, a labeling means for labeling said antibody or fragment thereof, and not including porphyrin or derivatives thereof.

2. The conjugated reagent of claim 1 wherein said antibody or fragment thereof has a specific affinity for insoluble cross-linked elastin and insoluble, cross-linked fragments thereof.

3. The conjugated reagent of claim 1 wherein said antibody or fragment thereof has an affinity for chondroitin sulfate proteoglycan.

4. The conjugated reagent of claim 1 where the labeling means is a radionuclide.

5. The conjugated reagent of claim 4 where the radionuclide is selected from the group of Co-57, Cu-67, Ga-67, Ga-68, Ru-97, Tc-99m, In-111, In-113m, I-123, I-125, I-131, Hg-197, Au-198, and Pb-203.

6. The conjugated reagent of claim 1 wherein the labeling means is a magnetic contrast agent capable of being detected by magnetic resonance imaging techniques.

7. The conjugated reagent of claim 6 wherein the magnetic contrast agent is selected from the group of gadolinium, copper, cobalt, nickel and manganese complexes.

8. The conjugated reagent of claim 1 in which said antibody or fragment thereof is selected from the group consisting of a polyclonal antibody and a monoclonal antibody.

9. The conjugated reagent of claim 8 wherein said fragments are Fab fragments.

10. A method for the detection of diseases of the vascular system including a symptomatic atherosclerosis, the method comprising:
(a) preparing a conjugate of an antibody or fragment thereof having an affinity for at least one arterial wall component being selected from the group consisting of insoluble, cross-linked elastin and insoluble, cross-linked fragments thereof, and chondroitin sulfate proteoglycans, and a labeling means for labeling said antibody or fragment thereof, said conjugate not including porphyrin or derivatives thereof, said labeling means being linked to said antibody or fragment thereof and capable of being detected extracorporeally;

(b) introducing the conjugate into the vascular system via a physiologically compatible vehicle in an amount effective for detection;

(c) detecting the location of the conjugate within the vascular wall with an extracorporeal detection means capable of detecting the labeling means; and (d) quantifying the conjugate concentration at at least one location in order to determine the presence and extent of vascular disease.

11. The method of claim 10 wherein the step of preparing a conjugate further includes employing an antibody or fragment thereof having a specific affinity for insoluble, cross-linked elastin and insoluble, cross-linked fragments thereof.

12. The method of claim 10 wherein the step of preparing a conjugate further includes employing an antibody or fragment thereof having an affinity for chondroitin sulfate proteoglycan.

13. The method of claim 10 wherein the step of preparing a conjugate further includes employing a radionuclide selected from the group of Co-57, Cu-67, Ga-67, Ga-68, Ru-97, Tc-99m, In-111, In-113m, I-123, I-125, I-131, Hg-197, Au-198 and Pb-203 as the labeling means.

14. The method of claim 10 wherein the step of preparing a conjugate further includes employing a monoclonal antibody or active fragment thereof.

15. The method of claim 10 wherein the step of preparing a conjugate further includes employing a polyclonal antibody or active fragment thereof.

16. The method of claim 10 wherein the step of preparing a conjugate further includes employing a radionuclide as the labeling means and the step of detecting the location of the conjugate within the vascular wall further includes detecting radiation therefrom with a radiation detector.

17. The method of claim 16 wherein the step of detecting radiation further includes employing a gamma camera to detect and make an image of gamma radiation emitted by the labeling means of the conjugate reagent.

* * * * *